United States Patent [19]
Ohki et al.

[11] Patent Number: 4,983,038
[45] Date of Patent: Jan. 8, 1991

[54] SHEATH FLOW TYPE FLOW-CELL DEVICE

[75] Inventors: Hiroshi Ohki, Tsuchiura; Ryo Miyake; Isao Yamazaki, both of Ibaraki; Fujiya Takahata, Katsuta, all of Japan

[73] Assignee: Hitachi, Ltd., Tokyo, Japan

[21] Appl. No.: 178,651

[22] Filed: Apr. 7, 1988

[30] Foreign Application Priority Data

Apr. 8, 1987 [JP] Japan ................................ 62-84751

[51] Int. Cl.$^5$ ............................................. G01N 21/05
[52] U.S. Cl. ..................................................... 356/246
[58] Field of Search ................. 356/73, 246, 336, 338, 356/339

[56] References Cited

U.S. PATENT DOCUMENTS

| | | | |
|---|---|---|---|
| 3,661,460 | 5/1972 | Elking et al. | 356/246 |
| 3,822,095 | 7/1974 | Hirschfeld | 356/39 |
| 3,873,204 | 3/1975 | Friedman et al. | 356/39 |
| 4,761,381 | 8/1988 | Blatt et al. | 356/246 |
| 4,804,267 | 2/1989 | Greenfield | 356/246 |

FOREIGN PATENT DOCUMENTS

| | | |
|---|---|---|
| 46345 | 2/1982 | European Pat. Off. |
| 125857 | 11/1984 | European Pat. Off. |
| 163206 | 12/1985 | European Pat. Off. |
| 200851 | 11/1986 | European Pat. Off. |
| 2521236 | 11/1976 | Fed. Rep. of Germany |
| 2543310 | 3/1977 | Fed. Rep. of Germany |
| 2853703 | 7/1980 | Fed. Rep. of Germany |
| 5415 | 3/1972 | Japan |
| 108877 | 8/1981 | Japan |

OTHER PUBLICATIONS

Kamentsky et al., "Spectrophotometer: New Instrument for Ultra Rapid Cell Analyses", *Science*, vol. 150 (Oct. 29, 1965), pp. 630–631.

Eisert et al., "Simple flow microphotometer for rapid cell population analysis," *Rev. Sci. Instrum.*, vol. 46, No. 8 (Aug. 1975), pp. 1021–1024.

Steinkamp, John A., "Flow Cytometry", *Rev. Sci. Instrum.*, 55(9), Sep. 1984, Section IID, Flow Chambers, pp. 1380–1381.

*Primary Examiner*—Richard A. Rosenberger
*Attorney, Agent, or Firm*—Antonelli, Terry, Stout & Kraus

[57] ABSTRACT

A sheath flow type flow-cell device for photo-particle-analyzer comprises a substantially flat top surface, at least one first inlet for sheath fluid, at least one first flow passage communicated with the at least one first inlet and contracted toward downstream to be a straight capillary flow passage, a discharge port provided at a terminal end of the straight capillary flow passage, a second inlet for sample fluid, a second flow passage for sample fluid communicated with the second inlet and contracted toward downstream, and coupling portions for sealingly coupling with the particle photo-analyzer. The second flow passage is opened within the at least one first flow passage so as to keep a part of the at least one first flow passage above and below an opening of the second flow passage. The opening is faced in the same direction as the straight capillary flow passage. A wall portion on which the opening locates is rounded. The wall portion is further chamfered and a pair of projections are extended from the wall portion.

18 Claims, 12 Drawing Sheets

SHEATH FLOW TYPE FLOW-CELL DEVICE

BACKGROUND OF THE INVENTION

The invention relates a sheath flow type flow-cell device for photo-particle-analyzers in which fluid carrying particles is made to flow in a capillary flow passage and a light beam is applied thereto and particle analysis is effected on the basis of the strength of the scattering light and/or fluorescence from the particles. The invention further relates to a photo-cell-analyzer and a photo-particle-detector using the flow-cell device.

Heretofore, in order to measure the number, kind, size or shape of particles such as blood cells, photo-particle-analyzers have been used in which fluid carrying particles is made to flow in a capillary flow passage and a light beam is applied thereto and on the basis of the strength of the scattering light and/or fluorescence from the particles, cell analysis, count of particles or the like is effected. In the cell analysis art, such photo-particle-analyzer is called a flow-cytometer. An example of the flow-cytometer is shown in SCIENCE, vol. 150, pages 630-631, 1965. The flow-cell device in the flow-cytometer, as shown in FIGS. 23 and 24, includes a thin bowtie-shaped flow passage. Only suspension of cells is made to flow in the flow passage. Therefore, the flow-cell device has often been clogged during use.

In order to solve the above-mentioned drawback, one method has been disclosed in U.S. Pat. No. 3,873,204. In the method, the suspension of cells (fluid carrying particles) is made to flow together with a physiological salt solution (a sheath fluid) in such a manner that the suspension of cells is surrounded by the physiological salt solution. This method is called as a sheath flow method. The sheath flow method is widely used in cell analyzers as an effective means. In the flow-cell device, a capillary flow passage is formed by a cylindrical glass tube. Therefore, the thickness of the flow-cell device becomes large. Moreover, the entrance portion of the glass tube is made in a funnel shape in order to provide for smooth non-turbulent flow of the fluid at the capillary flow passage, so that the capillary flow passage is made long, for example about 30mm, in order to avoid interference between the objective lens and the funnel-shaped portion of the glass tube. In general, the diameter of the capillary flow passage is made about $300 \times 10^{-6}$ m. Therefore, as the length of the capillary flow passage is made longer, the pressure loss becomes greater. Accordingly, the flow-cell device requires pump units having large capacity and a glass tube, piping and the like having high pressure resistance. This makes the flow-cell device itself and the photo-analyzer using the flow-cell device larger. Moreover, as the flow-cell device is made with glass tubes, it is difficult to make the flow-cell device precisely.

Another sheath flow method has also been proposed in Review of Scientific Instruments, Vol. 46, No. 8, pages 1021-1024, August 1975. In the method, the flow-cell device having two flow passages for sheath fluid is used. In the flow-cell device, a first sheath fluid is made to flow in the conical-shaped first flow passage so as to surround sample fluid and a second sheath fluid is made to flow in the conical-shaped second flow passage provided at the circumference of the first flow passage. The flow-cell device can make the flow of the sample fluid stabler but it also has the above-described drawbacks.

SUMMARY OF THE INVENTION

An object of the invention is to provide a sheath flow type flow-cell device for photo-particle-analyzers which can reduce the pressure loss in the capillary flow passage to thereby enable the fluid feeding system of the photo-particle-analyzers to be made with low pressure specifications.

Another object of the invention is to provide a sheath flow type flow-cell device which can be produced easily and precisely to thereby make the flow of the sample fluid stable.

Further another object of the invention is to provide a photo-cell-analyzer and a photo-particle-detector of which the fluid feeding systems are made to low pressure specifications and which are compact in size.

A sheath flow type flow-cell device for photo-particle-analyzer according to the invention comprises a substantially flat top surface, at least one first inlet for sheath fluid, at least one first flow passage which communicates with said at least one first inlet and is contracted toward a downstream portion to be a straight capillary flow passage, a discharge port provided at a terminal end of said straight capillary flow passage, a second inlet for sample fluid, a second flow passage for sample fluid communicated with said second inlet and contracted toward a downstream portion to be opened within said at least one first flow passage so as to keep a part of said at least one first flow passage above and below an opening of said second flow passage, said opening being faced in the same direction as said straight capillary flow passage, and coupling portions for sealingly coupling with said photo-particle-analyzer respectively provided at said first and second inlets and said discharge port.

A photo-cell-analyzer according to the invention comprises a first pump for feeding a suspension of cells; a diluting apparatus for diluting said suspension of cells and connected to said first pump; a dyeing apparatus for dyeing said suspension of cells and connected to said diluting apparatus; a second pump for feeding sheath fluid; a flow-cell device comprising a substantially flat top surface, at least one first inlet for sheath fluid, at least one first flow passage communicated with said at least one first inlet and contracted toward a downstream to portion be a straight capillary flow passage, a discharge port provided at a terminal end of said straight capillary flow passage, a second inlet for suspension of cells, a second flow passage for suspension of cells communicated with said second inlet and contracted toward a downstream portion to be opened within said at least one first flow passage so as to keep a part of said at least one first flow passage above and below an opening of said second flow passage, and said opening being faced in the same direction as said straight capillary flow passage, said at least one first inlet being connected to said second pump and said second inlet being connected to said dyeing apparatus; a light source for emitting a light beam; a condenser lens for applying said light beam to said suspension of cells in said capillary flow passage; an objective lens disposed on a side of said substantially flat top surface and collecting fluorescence and scattering light from said cells; half mirror for separating said fluorescence from said scattering light; a first photo-detector for detecting said scattering light; a second photo-detector for detecting said fluorescence; and a signal processor connected to said first and second photo-detectors.

A photo-particle-detector according to the invention comprises feeding means for feeding a fluid carrying particles; a pump for feeding sheath fluid, a flow-cell device comprising a substantially flat top surface, at least one first inlet, for sheath fluid, at least one first flow passage which communicates with said at least one first inlet and is contracted toward a downstream portion to be a straight capillary flow passage, a discharge port provided at a terminal end of said straight capillary flow passage, a second inlet for fluid carrying particles, a second flow passage for fluid carrying particles communicated with said second inlet and contracted toward a downstream portion to be opened within said at least one first flow passage so as to keep a part of said at least one first flow passage above and below an opening of said second flow passage, said opening being faced in the same direction as said straight capillary flow passage, said at least one first inlet being connected to said pump and said second inlet being connected to said feeding means; a light source for emitting a light beam; a condenser lens for applying said light beam on said fluid carrying particles in said capillary flow passage; an objective lens disposed on a side of said substantially flat top surface and collecting scattering light from said particles; a photo-detector for detecting said scattering light; and a signal processor connected to said photo-detector.

DETAILED DESCRIPTION OF THE PREFERRED EMBODIMENTS

Figure 1:
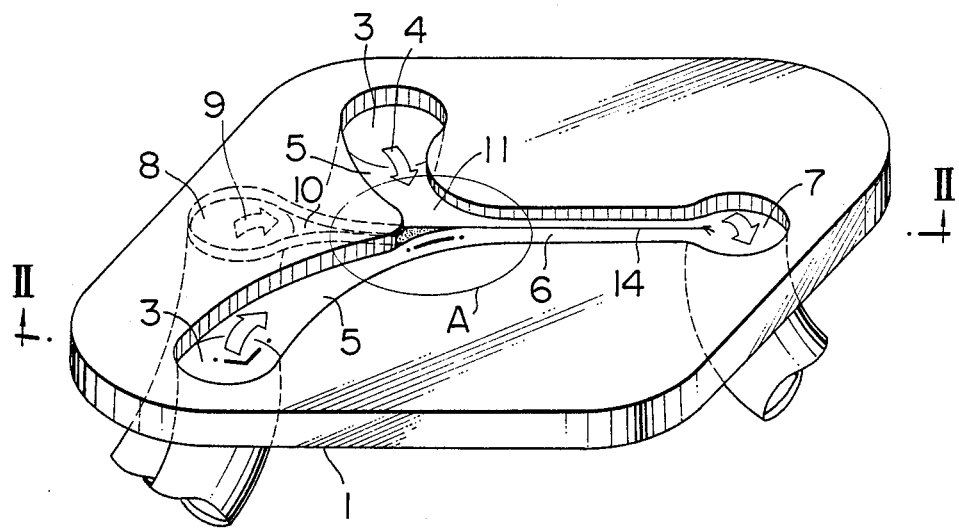
FIG. 1 is a schematic perspective view of an embodiment of a sheath flow type flow-cell device according to the invention of which top portion is omitted in order to show the interior thereof.
Figure 2A:
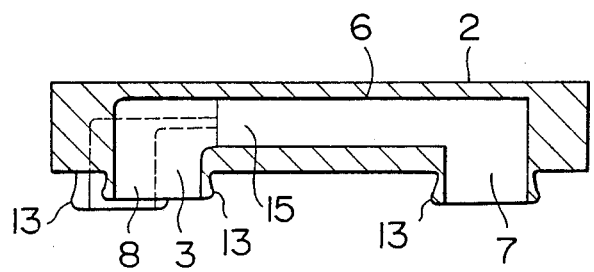
FIG. 2A is a sectional side view of the flow-cell device taken along line II—II in FIG. 1.
Figure 2B:
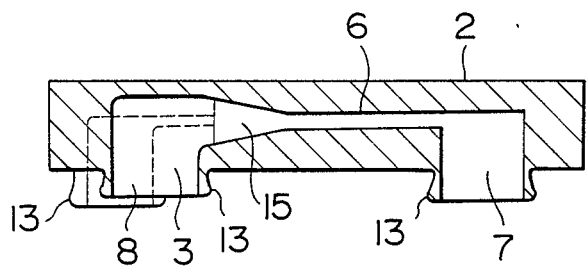
FIG. 2B is a sectional side view of a modification of the embodiment shown in FIG. 2A.
Figure 3:
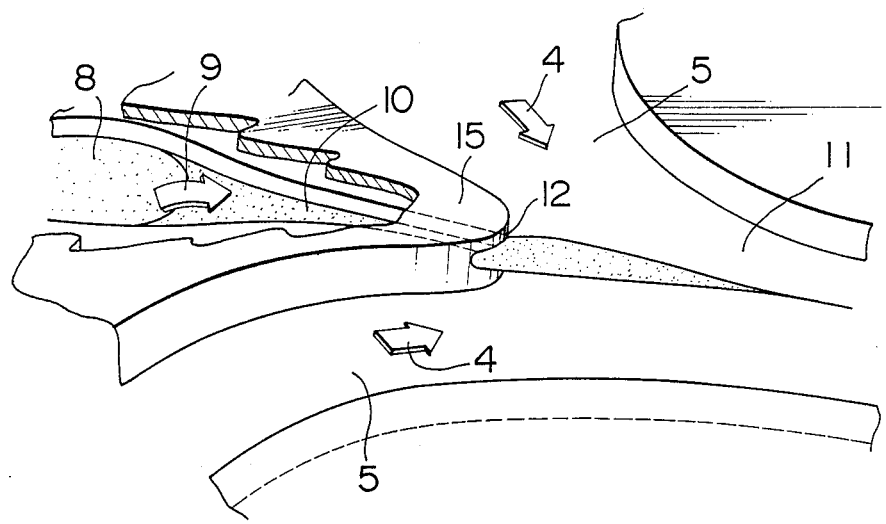
FIG. 3 is an enlarged perspective view of a portion A in FIG. 1.

Sheath flow type flow-cell devices according to the invention will be explained with reference to FIGS. 1-19. FIGS. 1-3 show an embodiment of the sheath flow type flow-cell devices of the invention a top portion of the flow-cell device 1 is made of a plate-like shape of which top surface 2 is substantially made flat. Two inlets 3 for sheath fluid 4 are provided on the lower side of the flow-cell device 1 and two flow passages 5 are communicates with the two inlets 3, respectively. The flow passages 5 are contracted toward a downstream portion thereof and join to become a straight capillary flow passage 6. In the embodiment shown in FIG. 2A, the flow passages 5 are contracted in the widthwise direction while in a modification shown in FIG. 2B, the flow passage 5 are contracted also in the heightwise direction. A top and a bottom side of the straight capillary flow passage 6 are transparent. The flow passages 5 and the capillary flow passage 6 have a substantially rectangular cross section. At a terminal end of the capillary flow passage 6, a discharge port 7 is provided. An inlet 8 for sample fluid 9 such a suspension of cells is provided between the two inlets 3 and on the lower side of the flow-cell device. A flow passage 10 is communicates with the inlet 8 and is contracted toward a downstream portion thereof. The flow passage 10 also has a substantially rectangular cross section. The flow passage 10 is opened within a junction 11 of the flow passages 5 for sheath fluid so as to keep a part of the flow passages 5 above and below an opening 12 thereof. The opening 12 is faced in the same direction as the straight capillary flow passage 6. Coupling portions 13 for sealingly coupling the flow-cell device 1 to a photo-particle-analyzer using the flow-cell device are respectively provided at the inlets 3, 8 and the discharge port 7.

The sheath fluid 4 such as physiological salt solution is introduced in the flow-cell device 1 from the two inlets 3. The sheath fluid 4 is contracted in the flow passages 5 and flows into the straight capillary flow passage 6 in a laminar flow condition. The sample fluid 9 is introduced into the flow-cell device 1 from the inlet 8. The sample fluid 9 is also contracted in the flow passage 10 and flows into the unction 11 of the flow passages 5. As a part of flow passages 5 is left above and below the opening 12, the sample fluid 9 is surrounded by the sheath fluid 4 from above and below in addition to the right and left direction in the straight capillary flow passage 6, the sample fluid 9 flows in a thin stream 14 at the center of the cross section of the capillary flow passage 6. As the thin stream 14 is a laminar flow, particles carried in the sample fluid 4, for example the cells in the suspension, flow one by one. A light beam from a light source not shown is applied on the sample fluid 9 in the thin stream 14 from below the flow-cell device and scattering light and/or fluorescence caused by the particles in the sample fluid is collected from an objective lens and particle analysis is effected on the basis of the scattering light and/or fluorescence. The sheath fluid 4 surrounding the sample fluid 9 passed through the capillary flow passage 6 is discharged from the discharge port 7.

Figure 4:
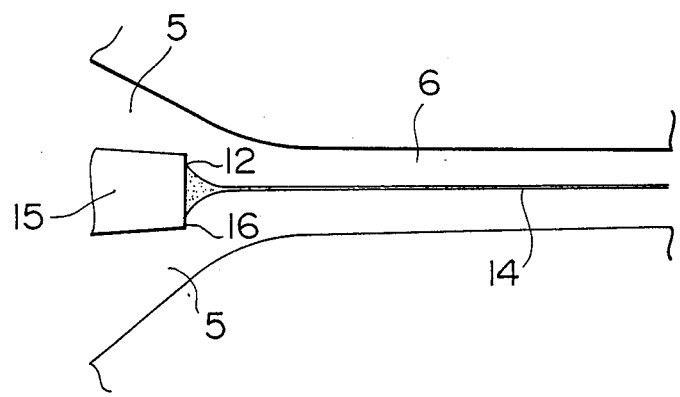
FIGS. 4—6 are schematic plan views showing flow condition in a capillary flow passage.
Figure 5:
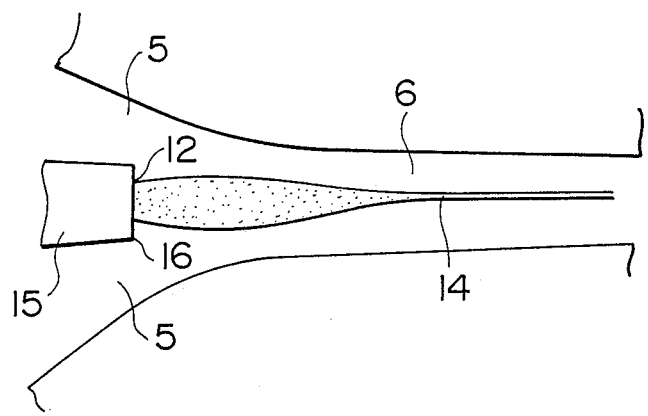
Figure 6:
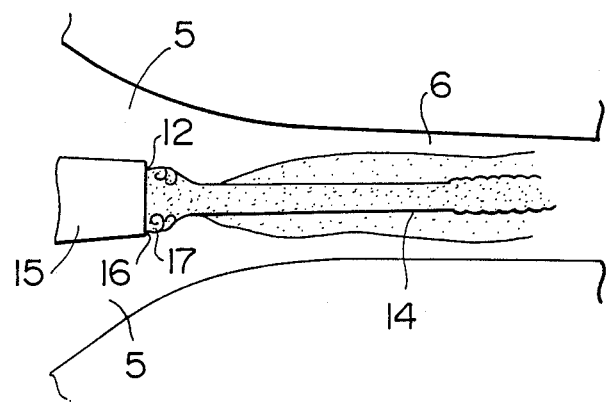
Figure 7:
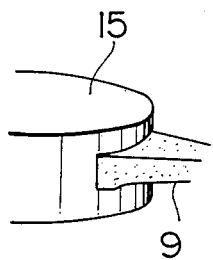
FIGS. 7—9 are schematic perspective views showing a wall portion on which the second flow passage is opened.
Figure 8:
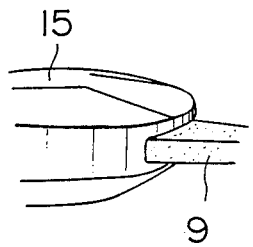
Figure 9:
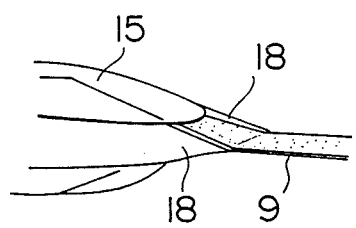
Figure 13:
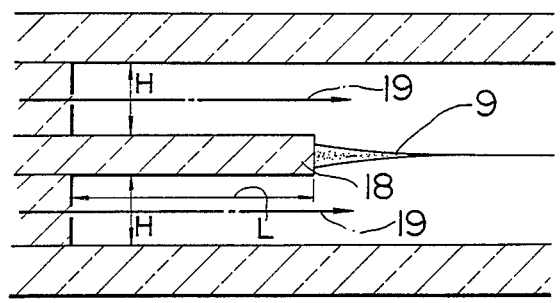
FIG. 13 is a schematic side view of the projections for explaining an effective length of the projections.
Figure 14:
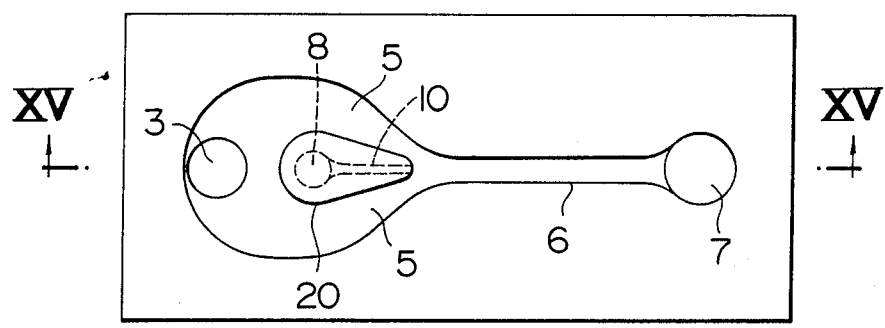
FIG. 14 is a sectional view of other embodiment of the flow-cell device according to the invention taken along line XIV—XIV in FIG. 15.
Figure 15:
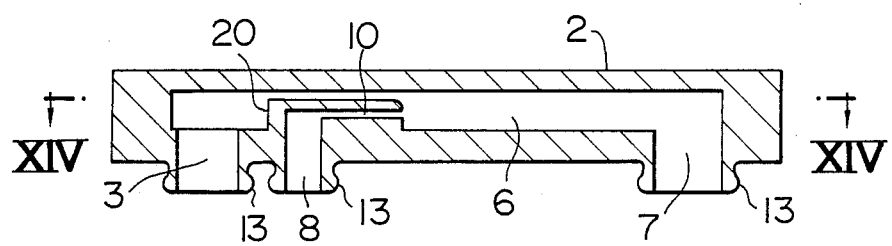
FIG. 15 is a sectional side view taken along line XV—XV in FIG. 14.
Figure 16:
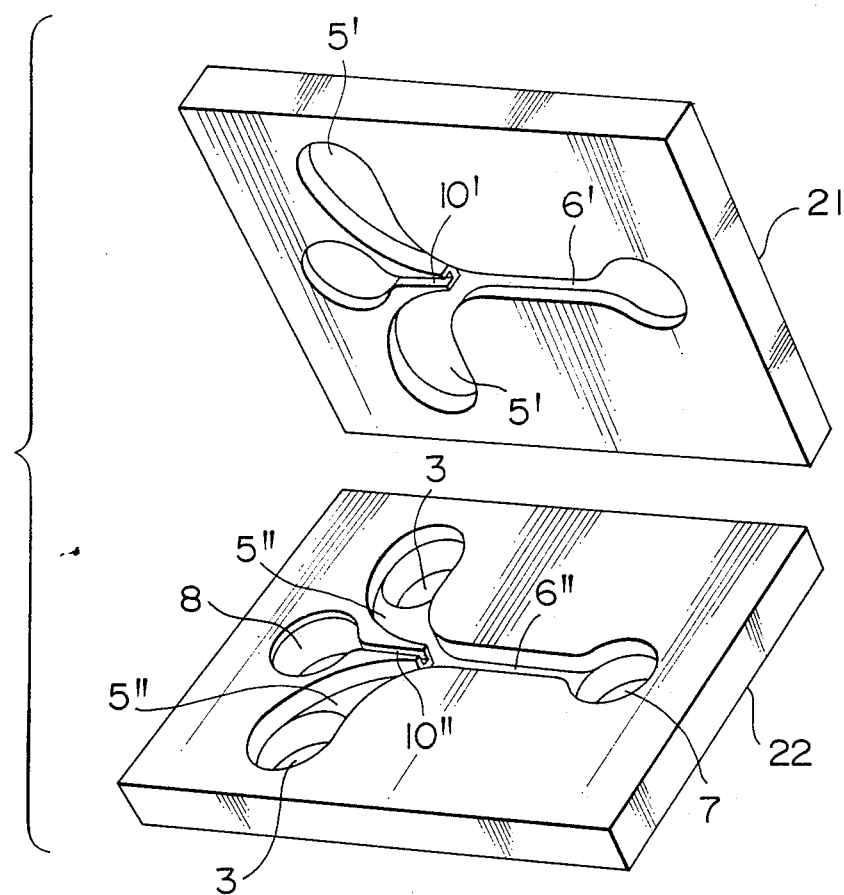
FIG. 16 is a perspective view of other embodiment of the flow-cell device according to the invention which is opened to explain the structure
Figure 17:
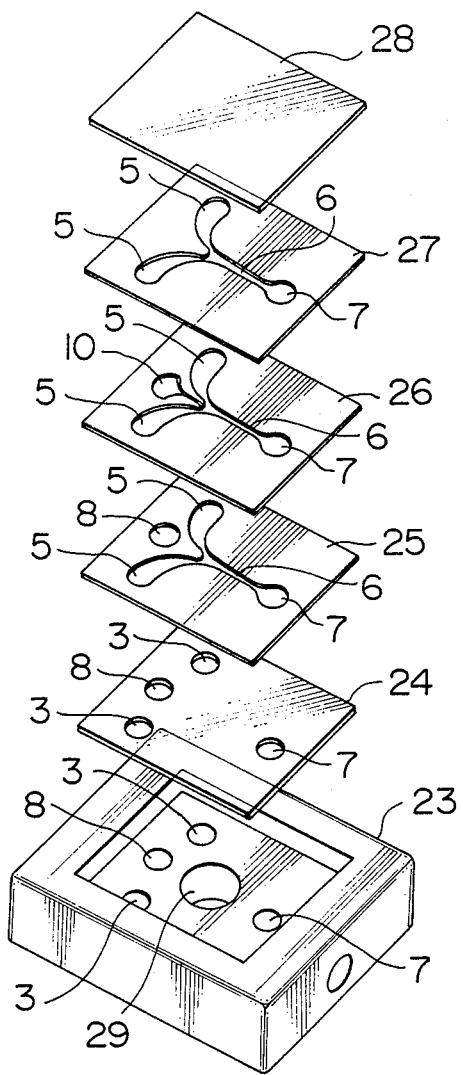
FIG. 17 is a perspective view of other embodiment of the flow-cell device according to the invention.
Figure 18:
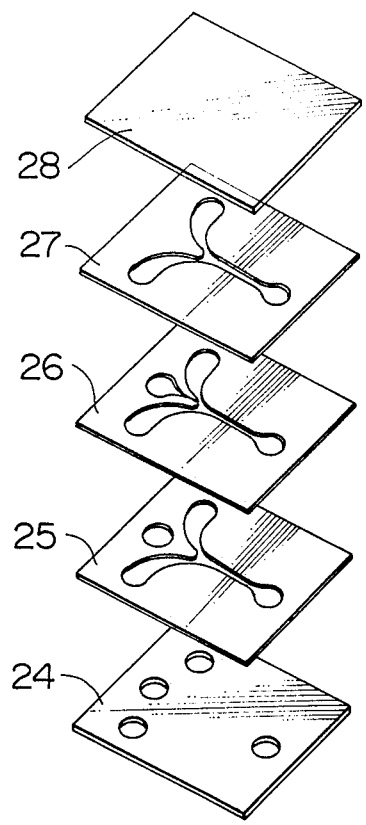
FIG. 18 is a perspective view of other embodiment of the flow-cell device according to the invention.
Figure 19:
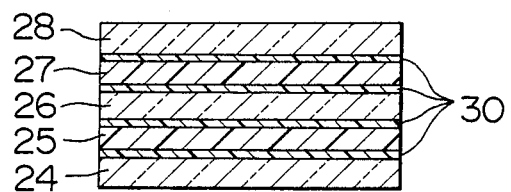
FIG. 19 is a schematic side view of the flow-cell device in FIG. 18.

Then, a relation between a wall portion 15 on which the opening 12 is located and a stability of the flow of the sample fluid 9 will be explained with reference to FIGS. 4-13. FIGS. 4-6 show flow conditions of the sample fluid 9 in a case where corners 16 are provided on the wall portion 15 and FIG. 4 shows a flow condition of the sample fluid 9 of which the flow rate is small; FIG. 5 shows a flow condition of the sample fluid 9 of which the −0 flow rate is middle; FIG. 6 shows a flow condition of the sample fluid 9 of which the flow rate is large. As shown in FIG. 4, the sample fluid 9 flows stably when the flow rate is small. As shown in FIG. 5, when the flow rate is middle, the sample fluid 9 spreads its width of the stream after flowing out the opening 12 but contracts its width promptly to flow in stable laminar flow. As shown in FIG. 6, when the flow rate is large, a wake 17 occurs at the corners 16 and the sample fluid 9 cannot flow stably. A limit on which the flow of the sample fluid is a stable laminar flow is referred to as a stable limit. It is necessary to make the stable limit large in order to analyze the sample fluid speedily. FIGS. 7-9 show modifications of the wall portion 15 to increase the stable limit. In a modification shown in FIG. 7, the wall portion 15 is rounded and there is no corner to produce the wake 17, so that the stable limit is increased. In a modification shown in FIG. 8, the wall portion 15 is rounded and moreover chamfered. On account of chamfering the wall portion 15, the sheath fluid 4 can easily flow into the upper and lower sides of the stream of the sample fluid 9 in laminar flow, so that the stable limit is further increased. In a modification shown in FIG. 9, a pair of tapered projections 18 are provided on the wall portion. As the tapered projections guide the sample fluid 9 flowing out of the flow passage 10, the sample fluid 9 becomes a flat and stable stream just at the opening 12, so that the stable limit is further increased. FIGS. 10-13 show a modification of the projections 18. A pair of plate-like projections 18 are extended from the wall portion 15 in the flow direction of the sample fluid 9. As shown in the drawings, clearances exist above and below the projections. Therefore, it is improved for the sheath fluid to flow above and below the flow of the sample fluid 9, so that the stable limit is further increased and the stream of the sample fluid becomes flatter. The flat stream of the sample fluid is preferable to the blood cell analysis, since flat cells such as red blood cells are aligned in the same attitude to be made to flow. In FIG. 13, the character L denotes the height of the clearances. In the cell analysis, it is preferable that the height of clearances is 100-500 μm and a ratio of L/H is five and over.

According to the embodiment including the modifications, as the top surface of the flow-cell device is made substantially flat, the interference between the flow-cell device and the objective lens can be avoided and it is possible to locate the focus of the objective lens on a place where the thin and stable stream of the sample fluid is just formed by the capillary flow passage. Accordingly, it is not necessary to lengthen the capillary flow passage like the prior art flow-cell devices and the length of the capillary flow passage of the invention may be a necessary minimum length. As a great part of the pressure loss in the flow-cell device is resulted from the capillary flow passage, the shorter the length of the capillary flow passage becomes, the smaller the pressure loss becomes. Practically, the length of the capillary flow passage of the embodiment may be 2-3mm and therefore the pressure loss is reduced to the degree of 1/10 of the prior art. This enables the capacity of the pumps for feeding the sample fluid and the sheath fluid to become small and the strength of the pressure resistance of the flow system to become small and further the photo-particle-analyzer to become small.

Figure 20:
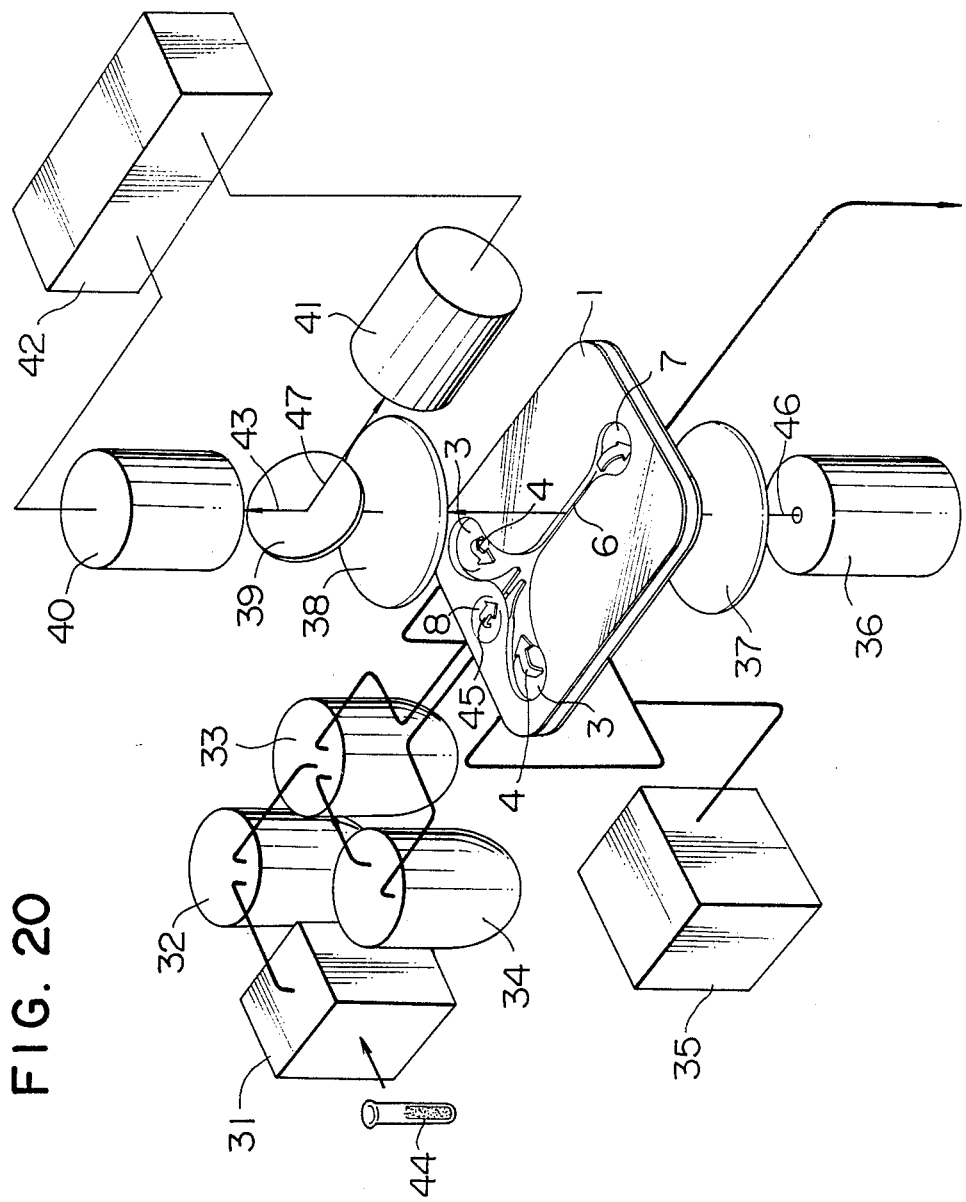
FIG. 20 is a schematic perspective view of a photo-cell-analyzer according to the invention.

FIG. 20 shows a photo-cell-analyzer according to the invention. The photo-cell-analyzer comprises a flow system and an optical system.

Figure 10:
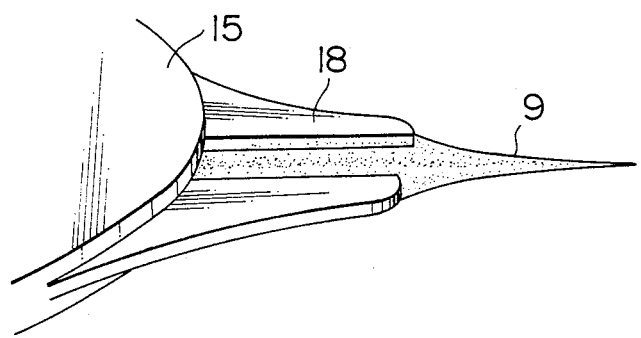
FIG. 10 is a perspective view of a pair of projections provided on the wall portion.
Figure 11:
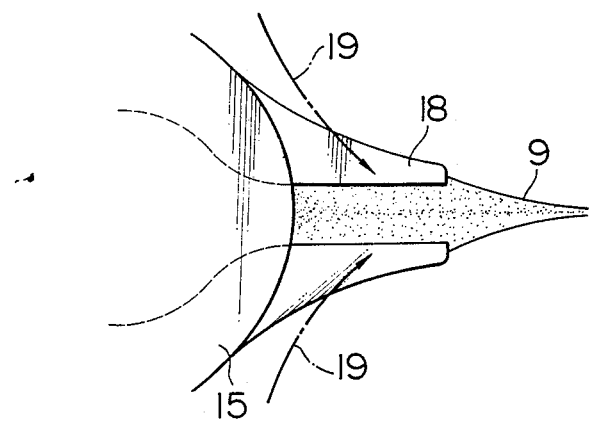
FIG. 11 is a plan view of the projections.
Figure 12:
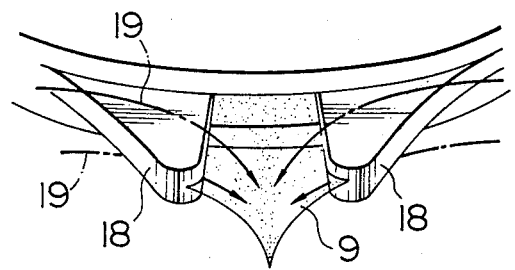
FIG. 12 is a front view of the projections.

The flow system comprises a first pump 31 for feeding a suspension of cells 44, a diluting apparatus 32 for diluting the suspension of cells 44 and connected to the first pump 31, a dyeing apparatus 33 for dyeing the suspension of cells 44 and connected to the diluting apparatus 32, a second pump 35 for feeding a sheath fluid 4, a flow-cell device 1. In the embodiment, the flow-cell device shown in FIG. 1 with the projections shown in FIG. 10 is used. The two inlets 3 of the flow-cell device 1 are connected to the second pump 35 and the inlet 8 is connected to the dyeing apparatus 33. The suspension of cells 44 is fed t the inlet 8 of the flow-cell device 1 to be made to flow in the capillary flow passage 6 in laminar flow condition. The cells in the suspension 44 flow one by one with aligned in the same attitude in the capillary flow passage 6. The sheath fluid 4 is fed by the second pump 35 to the inlets 3 of the flow-cell device 1 and surrounds the suspension of cells 44 to flow in the capillary flow passage 6.

The optical system comprises a light source 36 for emitting a light beam 46, a condenser lens 37 disposed between the light source 36 and the flow-cell device 1, an objective lens 38 disposed on a side of the substantially flat top surface of the flow-cell device 1, a half mirror 39, a first photo-detector 40, a second photo-detector 41, and a signal processor 42 connected to the first and second photo-detectors. The condenser lens 37 applies the light beam 46 on the cells flowing in the capillary flow passage 6 and the objective lens 38 collects scattering light and fluorescence caused by the cells. The half mirror 39 separates the scattering light 43 from the fluorescence 47. The first photo-detector 40 detects the scattering light 43 to convert into electric signals. The second photo-detector 41 detects the fluorescence to convert into electric signals. The signal processor 42 conducts the cell-analysis from the electric signals.

The photo-cell-analyzer may include a hemolysis apparatus 34 arranged between the dyeing apparatus 33 and the inlet 8 of the flow-cell device 1. In such a case, the piping between the dyeing apparatus 33 and the inlet 8 is closed.

As the flow-cell device 1 can reduce the pressure loss, the elements used in the flow system such as the first and second pumps 31, 35 can be low-pressure specification. Accordingly, the photo-cell-analyzer can be a compact size.

Figure 21:
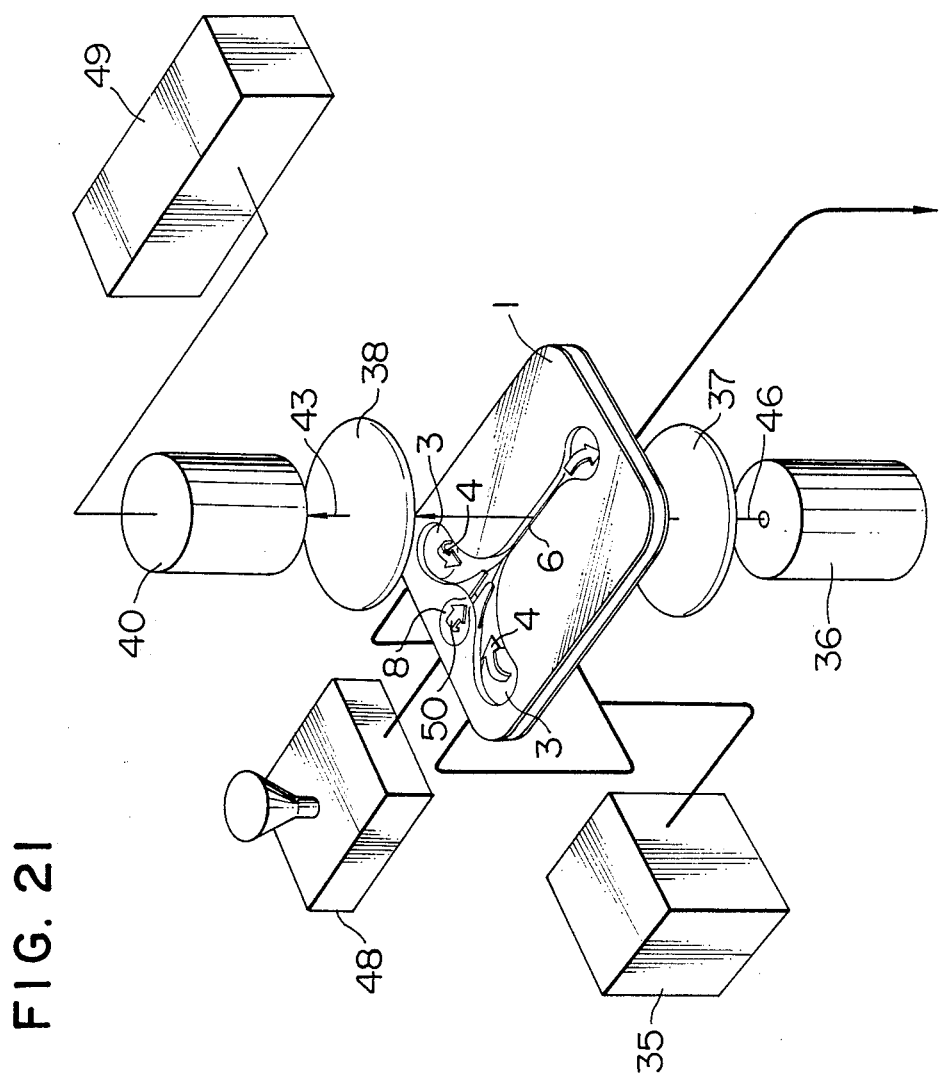
FIG. 21 is a schematic perspective view of a photo-particle-detector according to the invention.

FIG. 21 shows a photo-particle-detector according to the invention. The photo-particle-detector comprises a flow system and an optical system.

The flow system comprises a feeding apparatus 8 for feeding fluid carrying particles 8, a pump 35 for feeding sheath fluid and a flow-cell device 1. In the embodiment, the flow-cell device shown in FIG. 1 with projections shown in FIG. 10 is used. The feeding apparatus 48 is connected to the inlet 8 of the flow-cell device 1 and the pump 35 is connected to the inlets of the flow-cell device 1. The fluid carrying particles 50 is fed to the inlet 8 of the flow-cell device 1 to be made to flow in the capillary flow passage 6 in laminar flow condition. The particles in the fluid 50 flow one by one with aligned in the same attitude in the capillary flow passage 6. The sheath fluid 4 is fed by the pump 35 to the inlets 3 of the flow-cell device and surrounds the fluid carrying particles to flow in the capillary flow passage 6.

The optical system comprises a light source 36 for emitting a light beam 46, a condenser lens 37 disposed between the light source 36 and the flow-cell device 1, an objective lens 38 disposed on a side of the top surface of the flow-cell device 1, a photo-detector 40, and a signal processor 49 connected to the photo-detector 40. The condenser lens 37 applies the light beam 46 on the particles flowing in the capillary flow passage 6 and the objective lens 38 collects scattering light caused by the particles. The photo-detector 40 detects the scattering light 43 to convert into electric signals. The signal processor 49 detects the number of the particles from the electric signals. In a case where the photo-particle-detector is used as a dust counter for air, the fluid carrying particles 50 may be air and the sheath fluid 4 may be clean air. In a case where the photo-particle-detector is used as a dust counter for water, the fluid carrying particles may be water and the sheath fluid may be pure water or clean air.

As the flow-cell device 1 can reduce the pressure loss, the elements used in the flow system such as pumps 35 can be low-pressure specification. Accordingly, the photo-particle-detector can be a compact size.

Figure 22:
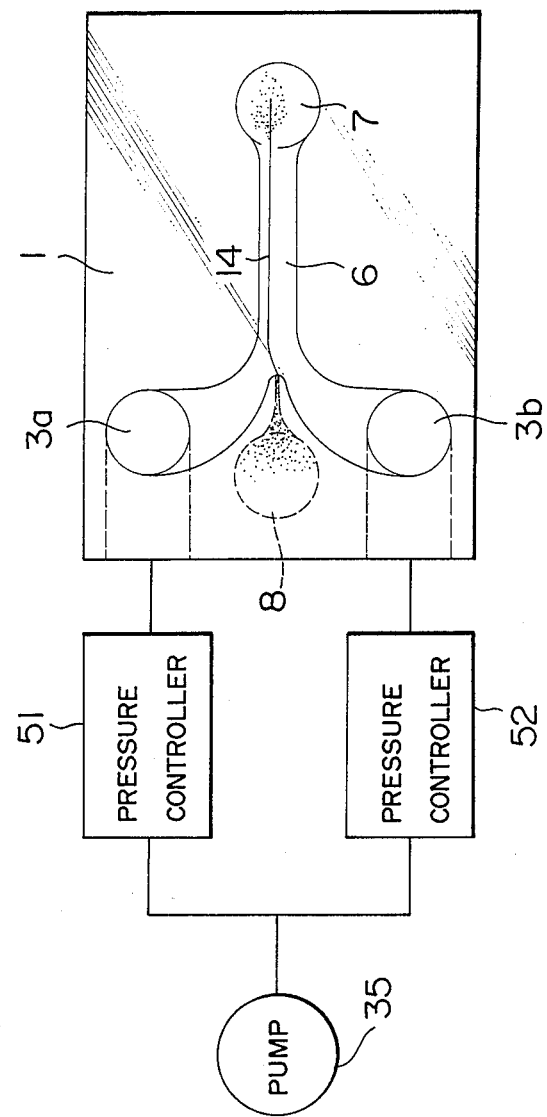
FIG. 22 is a schematic plan view of a part of the photo-cell-analyzer in FIG. 20 or the photo-particle-detector in FIG. 21.
Figure 23:
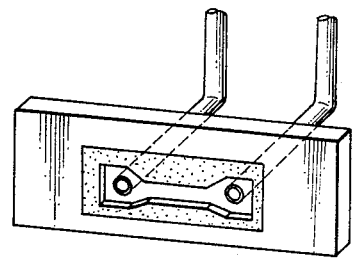
FIG. 23 is a perspective view of a prior art flow-cell device.
Figure 24:
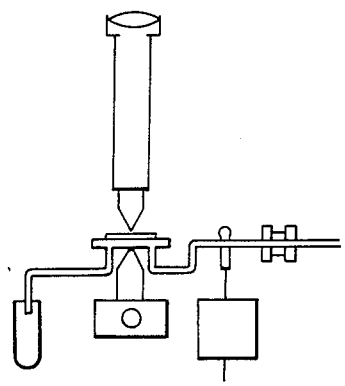
FIG. 24 is a side view of a prior art photo-cell-analyzer.

FIG. 22 shows a modification of the flow system of the photo-cell-analyzer shown in FIG. 20 or the photo-particle-detector shown in FIG. 21. The flow-cell device 1 has the same structure as the embodiment shown in FIG. 1. A pressure controller 51 is provided between the pump 35 and the inlet 3a of the flow-cell device 1 and another pressure controller 52 is provided between the pump 35 and the inlet 3b of the flow-cell device 1. In the previously described embodiments, the pressure of the sheath fluid flowing into one inlet 3a and the pressure of the sheath fluid flowing into the other inlet 3b are identical with each other. In the present modification, the pressure of the sheath fluid flowing into each of the inlets is adjustable. In FIG. 22, the pressure of the sheath fluid flowing into the inlet 3a is made lower than the sheath fluid flowing into the other inlet 3b, so that the stream 14 of the fluid carrying particles is shifted to a side of the sheath fluid flowing from the inlet 3a.

On account of the structure, it becomes possible to adjust the position of the stream of the fluid carrying particles in the capillary flow passage 6. This characteristic is useful for the photo-particle-detector and the photo-cell-analyzer, since when the position of the light beam is shifted from the stream of the fluid carrying particles by any cause, it is easily possible to locate the stream of the fluid carrying particles on the light beam by adjusting the pressure of the sheath fluid of each of the inlets 3a, 3b.

What is claimed is:

1. A sheath flow type flow-cell device for a photo-particle-analyzer comprising:
   a substantially flat top surface;
   at least one first inlet for sheath fluid;
   at least one first flow passage having a substantially rectangular cross-section and communicated with said at least one first inlet and contracted only in a widthwise direction of said flow-cell device toward a downstream portion to form a straight capillary flow passage having a substantially rectangular cross-section;
   a discharge port provided at a terminal end of said straight capillary flow passage;
   a second inlet for sample fluid; and
   a second flow passage for said sample fluid communicated with said second inlet and contracted toward a downstream portion to be opened within said at least one first flow passage so as to keep a part of said at least one first flow passage above and below an opening of said second flow passage, said opening being faced in the same direction as said straight capillary flow passage.

2. A sheath type flow-cell device for a photo-particle-analyzer according to claim 1, wherein said at least one first flow passage having a substantially rectangular cross-section enables said flow-cell device to substantially eliminate interference between said flow-cell device and an objective lens system for observing said sample fluid, thereby enabling said capillary flow passage to become a minimum length.

3. A sheath flow type flow-cell device for a photo-particle-analyzer comprising:
   a substantially flat top surface;
   at least one first inlet for sheath fluid;
   at least one first flow passage communicated with said at least one first inlet and contracted toward a downstream portion to form a straight capillary flow passage;
   a discharge port provided at a terminal end of said straight capillary flow passage;
   a second inlet for sample fluid; and
   a second flow passage for sample fluid communicated with said second inlet and contracted toward a downstream portion to be opened within said at least one first flow passage so as to keep a part of said at least one first flow passage above and below an opening of said second flow passage, said opening being faced in the same direction as said straight capillary flow passage, wherein a wall portion containing said opening of said second flow passage is rounded and defines a sample fluid port.

4. A sheath flow type flow-cell device as claimed in claim 3, wherein said wall portion is chamfered.

5. A sheath flow type flow-cell device as claimed in claim 4, further comprising a pair of projections for guiding a flow of said sample fluid in said at least one first flow passage, said pair of projections extending from said wall portion.

6. A sheath flow type flow-cell device as claimed in claim 3, further comprising a pair of projections for guiding a flow of said sample fluid in said at least one first flow passage, said pair of projections extending from said wall portion.

7. A sheath flow type flow-cell device for a photo-particle-analyzer comprising:
   a substantially flat top surface;
   at least one first inlet for sheath fluid;
   at least one first flow passage communicated with said at least one first inlet and contracted toward a downstream portion to form a straight capillary flow passage;
   a discharge port provided at a terminal end of said straight capillary flow passage;
   a second inlet for sample fluid; and
   a second flow passage for sample fluid communicated with said second inlet and contracted toward a downstream portion to be opened within said at least one first flow passage so as to keep a part of said at least one first flow passage above and below an opening of said second flow passage, said opening being faced in the same direction as said straight capillary flow passage, wherein said flow-cell device is formed by upper and lower plates; said upper plate being formed with a part of said at least one first flow passage, a part of said second flow passage, and a part of said capillary flow passage, said lower plate being formed with the other part of said at least one first flow passage, the other part of said second flow passage, said at least one first inlet, said second inlet and said discharge port.

8. A sheath flow type flow-cell device for a photo-particle-analyzer comprising:
a substantially flat top surface;
at least one first inlet for sheath fluid;
at least one first flow passage communicated with said at least one first inlet and contracted toward a downstream portion to form a straight capillary flow passage;
a discharge port provided at a terminal end of said straight capillary flow passage;
a second inlet for sample fluid; and
a second flow passage for sample fluid communicated with said second inlet and contracted toward a downstream portion to be opened within said at least one first flow passage so as to keep a part of said at least one first flow passage above and below an opening of said second flow passage, said opening being faced in the dame direction as said straight capillary flow passage, wherein said flow-cell device comprises a plurality of laminated plates on which are formed respective predetermined patterns which form said at least one first inlet, said at least one first flow passage, said discharge port and said second flow passage when said plurality of plates are overlapped with each other.

9. A sheath flow type flow-cell device as claimed in claim 8, wherein said plurality of laminated plates are made of glass.

10. A sheath flow type flow-cell device as claimed in claim 8, said plurality of laminated plates are made of glass plates and synthetic resin plates such as polyimide and said glass plates and said synthetic resin plates are disposed alternately.

11. A photo-cell analyzer comprising:
a first pump for feeding suspension of cell;
a diluting apparatus for diluting said suspension of cells and connected to said first pump;
a dyeing apparatus for dyeing said suspension of cells and connected to said diluting apparatus;
a second pump for feeding sheath fluid;
a flow-cell device comprising a substantially flat top surface, at least one first inlet for sheath fluid, at least one first flow passage having a substantially rectangular cross-section and communicated with said at least one first inlet and contracted only in the widthwise direction of the flow-cell device and toward a downstream portion to form a straight capillary flow passage having a substantially rectangular cross-section, a discharge port provided at a terminal end of said straight capillary flow passage, a second inlet for suspension of cells, a second flow passage for suspension of cells communicated with said second inlet and contracted toward a downstream portion to be opened within said at least one first flow passage so as to keep a part of said at least one first flow passage above and below an opening of said second flow passage, said opening being faced in the same direction as said straight capillary flow passage, said at least one first inlet being connected to said second pump and said second inlet being connected to said dyeing apparatus;
a light source for emitting a light beam;
a condenser lens for applying said light beam on said suspension of cells in said capillary flow passage;
an objective lens disposed on a side of said substantially flat top surface and collecting fluorescence and scattering light from said cells, a half mirror for separating said fluorescence from said scattering light;
a first photo-detector for detecting said scattering light;
a second photo-detector for detecting said fluorescence; and
a signal processor connected to said first and second photo-detectors.

12. A photo-cell-analyzer as claimed in claim 11, further comprising a hemolysis apparatus arranged between said dyeing apparatus and said second inlet of said flow-cell device.

13. A photo-cell-analyzer as claimed in claim 12, wherein said at least one first inlet comprises two inlets and two pressure controllers are respectively connected to said two inlets.

14. A sheath type flow-cell device for a photo-particle-analyzer according to claim 11, wherein said at least one first flow passage having a substantially rectangular cross-section enables said flow-cell device to substantially eliminate interference between said flow-cell device and said objective lens, thereby enabling said capillary flow passage to become a minimum length.

15. A photo-particle-detector comprising
feeding means for feeding fluid carrying particles;
a pump for feeding sheath fluid;
a flow-cell device comprising a substantially flat top surface, at least one first inlet for sheath fluid, at least one first flow passage having a substantially rectangular cross-section and communicated with said at least one first inlet and contracted only in the widthwise direction of the flow-cell capillary flow passage having a substantially rectangular cross-section, a discharge port provided at a terminal end of said straight capillary flow passage, a second inlet for fluid carrying particles, a second flow passage for fluid carrying particles communicated with said second inlet and contracted toward a downstream portion to be opened within said at least one first flow passage so as to keep a part of said at least one first flow passage above and below an opening of said second flow passage, said opening being faced in the same direction as said straight capillary flow passage, said at least one first inlet being connected to said pump and said second inlet being connected to said feeding means;
a light source for emitting a light beam;
a condenser lens for applying said light beam on said fluid carrying particles in said capillary flow passage;
an objective lens disposed on a side of said substantially flat top surface and collecting scattering light from said particles;

a photo-detector for detecting said scattering light; and a signal processor connected to said photo-detector.

16. A sheath type flow-cell device for a photo-particle-analyzer according to claim 15, wherein said at least one first flow passage having a substantially rectangular cross-section enables said flow-cell device to substantially eliminate interference between said flow-cell device and said objective, thereby enabling said capillary flow passage to become a minimum length.

17. A sheath flow type flow-cell device for a photo-particle-analyzer comprising:
- a substantially flat top surface;
- at least one first inlet for sheath fluid;
- at least one first flow passage communicated with said at least one first inlet and contracted in the widthwise direction of the flow-cell device and toward a downstream portion to form a straight capillary flow passage having a substantially rectangular cross-section;
- a discharge port provided at a terminal end of said straight capillary flow passage;
- a second inlet for sample fluid; and
- a second flow passage for sample fluid communicated with said second inlet and contracted toward a downstream portion to be opened within said at least one first flow passage so as to keep a part of said at least one first flow passage above and below an opening of said second flow passage, said opening being faced in the same direction as said straight capillary flow passage, said second flow passage being a flat passage for making the sample fluid flow flat.

18. A photo-particle-detector comprising:
- feeding means for feeding fluid carrying particles;
- a pump for feeding sheath fluid;
- a flow-cell device comprising a substantially flat top surface, two first inlets for sheath fluid, two first flow passages respectively communicated with said two first inlets and contracted in the widthwise direction of the flow-cell device toward a downstream portion and joined to form a straight capillary flow passage having a substantially rectangular cross-section, a discharge port provided at a terminal end of said straight capillary flow passage, a second inlet for fluid carrying particles, a second flow passage for fluid carrying particles communicated with said second inlet and contracted toward a downstream portion, said second flow passage being opened within a joining portion at which said two first flow passages are joined, said two first inlets being connected to said pump and said second inlet being connected to said feeding means;
- two pressure controllers respectively connected to said two first inlets for independently controlling pressure of the sheath fluid flowing in said two first flow passages to adjust the position of the sample fluid flow;
- a light source for emitting a light beam;
- a condenser lens for applying said light beam to said fluid carrying particles in the capillary flow passage;
- an objective lens disposed on a side of said substantially flat top surface and collecting scattering light from said particles;
- a photo-detector for detecting said scattering light; and
- a signal processor connected to said photo-detector.

* * * * *